United States Patent [19]
Iwakawa et al.

[11] Patent Number: 5,902,597
[45] Date of Patent: May 11, 1999

[54] UNDER FLOOR INSECT CONTROL METHOD FOR RESIDENTIAL STRUCTURES

[75] Inventors: Toru Iwakawa; Tamotsu Hirahara, both of Tokyo, Japan

[73] Assignee: Nippon Eisei Center Co., Ltd, Tokyo, Japan

[21] Appl. No.: 08/703,473

[22] Filed: Aug. 27, 1996

Related U.S. Application Data

[63] Continuation of application No. 08/449,337, May 24, 1995, abandoned.

[51] Int. Cl.$^6$ .............................. A01N 25/16; A01N 25/08
[52] U.S. Cl. ............................................ 424/409; 514/945
[58] Field of Search ................................................ 424/409

[56] References Cited

U.S. PATENT DOCUMENTS

| | | |
|---|---|---|
| 4,143,010 | 3/1979 | Rak . |
| 4,389,446 | 6/1983 | Blom et al. . |
| 4,421,788 | 12/1983 | Kramer . |
| 4,809,462 | 3/1989 | Maeda ........................................ 43/124 |
| 4,874,641 | 10/1989 | Kittle . |
| 4,889,710 | 12/1989 | Hagarty ....................................... 424/45 |
| 5,026,735 | 6/1991 | Stein . |
| 5,124,363 | 6/1992 | Stein . |
| 5,133,933 | 7/1992 | McIntosh . |
| 5,215,786 | 6/1993 | Kittle . |
| 5,284,844 | 2/1994 | Lorenz et al. . |
| 5,346,699 | 9/1994 | Tiernan et al. ......................... 424/405 |

OTHER PUBLICATIONS

Japanese Laid Open Patent No. 59–55940 (Iwakawa et al).
Higaki, "Clean Barrier Method and Its Effects" Kankyo-Kanri–Gijutsu, vol. 5, No. 4, pp. 194–198 (1987).

*Primary Examiner*—Peter F. Kulkosky
*Attorney, Agent, or Firm*—Smith, Gambrell & Russell, LLP; Beveridge, DeGrandi, Weilacher & Young Intellectual Property Group

[57] ABSTRACT

An under floor insect control method for structures in which an insect control chemical in a mixed resin foam coating is installed under the floor by forcefully mixing, at a nozzle part of the sprayer, and spraying on the soil surface the following: an aqueous emulsion, of which 15–20 percentage by weight is a solid copolymeric resin, based on vinyl acetate and alkyl methacrylate in a proportion ranging from 55–85 and 15–45 parts by weight, respectively; an inert organic solvent solution contains a mixture of diisocyanate and polypropylene glycol in a proportion ranging from 5–15 and 85–95 parts by weight, respectively. The two components make up an adjusted 60–80 percentage by weight as a total volume. An insect control chemical is also included. The proportion of organic solvent solution to the emulsion is in the range of 7–15 percentage by volume. The mixed resin foam insect control barrier formed provides superior insect control chemical immobilization, gas barrier and crack proof properties.

9 Claims, No Drawings

UNDER FLOOR INSECT CONTROL METHOD FOR RESIDENTIAL STRUCTURES

This application is a continuation of application Ser. No. 08/449,337, filed May 24, 1995, now abandoned, which application is entirely incorporated herein by reference.

BACKGROUND OF THE INVENTION

This invention relates to under floor insect control methods for residential structures, especially a method to protect wooden structures from termites and other wood-decaying injurious insects.

In conventional termite control methods for wooden structures, insect control chemicals containing emulsions or liquid concentrates are sprayed on the under floor soil and on the column surfaces of structures. These methods, however, do not permanently immobilize the insect control chemicals and do not provide prolonged insect control effects because the insect control ingredients evaporate in a relatively short time period. In order to improve permanent immobilization, certain insect control methods have been developed. For instance, in one method a hardened resin foam coated isolation layer, a barrier layer, containing an insect control chemical is formed by forcefully mixing a main solution (the asphalt emulsion modified polyvinyl acetate resin emulsion, which is a mixture of polyvinyl acetate resin emulsion and asphalt emulsifiable concentrates at about 7:3 proportion) containing an insect control chemical and an organic solvent solution (in which hydrophilic low molecular weight polyurethane resin is dissolved by methyl ethyl ketone or other organic solvents). The mixture is then sprayed on the structure's under floor soil surface.

Asphalt emulsion concentrate is a highly viscous black colored material and the main solution in the above instance, the asphalt emulsion modified polyvinyl acetate resin, is also black. The equipment and tools for spraying this mixture are quickly blackened and dirtied. Operators must be extremely careful when handling and spraying the mixture because their work clothes cannot be cleaned completely if soiled by the mixture. Therefore, work efficiency is significantly reduced. Asphalt emulsion concentrate, because it is usually a cationic surface active agent-based oil-in-water type emulsion formula, is susceptible to emulsion destruction when in contact with an anionic surface active agent. Therefore, it causes condensation and separation of emulsified-dispersed asphalt. Thus, it significantly restricts the choice of emulsion concentrate used for aqueous polyvinyl acetate resin emulsion. In addition, asphalt is principally composed of hydrocarbons and thus melts rubber packing and other materials used in the spraying equipment and tools. And, polyvinyl acetate emulsion increases the viscosity of added asphalt emulsion, thus making handling of the main solution more difficult.

The mixed resin foam coating layer formed by mechanically and forcefully mixing the asphalt emulsion modified polyvinyl acetate resin and organic solvent solution of hydrophilic polyurethane resin and by spraying it embeds and immobilizes the insect control ingredient which is mixed and sprayed together. The dried coating layer thereby formed, however, gradually contracts over time apparently due to the property of asphalt emulsion and creates, for instance, cracks and gaps several years later. The performance of the layer at that point is significantly reduced and the insect control effects are greatly diminished.

The inventors of this invention have repeatedly test produced various synthetic resin based aqueous emulsions and conducted application experiments to devise methods to solve the above mentioned problems. They have paid special attention to materials that can replace the asphalt emulsion. As a result, the inventors discovered that the mixed resin foam layer keeps the insect control chemical stable and immobilized for a long time period, allows little contraction over time, and effectively prevents cracks even if a slight contraction occurs because of the flexibility of soft to semi hard polyurethane resin. This layer is formed by spraying, along with an insect control chemical, a mixture of an aqueous emulsion, which is a copolymeric resin of a methacrylic ester based monomer and vinyl acetate (hereinafter referred to as "main solution"), and an organic solvent solution made of a polyurethane resin forming diisocyanate and polypropylene glycol.

SUMMARY OF THE INVENTION

The purpose of this invention, therefore, is to provide a buffer layer that has the flexibility and non-contraction property to prevent cracks over time, and which is physically stable enough to practically isolate the under floor space from the soil surface over a long time period. Another purpose of the invention is to provide an under floor insect control method that has superior operability and easier handling. In addition, the invention provides a practical and desirable insect control buffer that can keep the insect control chemical ingredients immobilized in a stable condition over a long time period and eliminate chances of termites or other microorganisms eating through and surfacing above the buffer. Technical characteristics and superior effects of the invention's method are described in the following.

This invention concerns primarily an under floor insect control method for structures in which an insect control chemical in a mixed resin foam coating can be installed under the floor by forcefully mixing, at a nozzle part of a sprayer, and spraying on the soil surface the following: an aqueous emulsion, of which 15–20 percentage by weight can be a solid resin of the copolymeric resin, containing vinyl acetate and an alkylmethacrylate in a proportion ranging from 55–85 and 15–45 parts by weight, respectively; an inert organic solvent solution of a mixture of diisocyanate and polypropylene glycol in a proportion ranging from 5–15 and 85–95 parts by weight, respectively, which comprise an adjusted 60–80 percentage by weight as a total volume of the two ingredients; and an insect control chemical. The proportion of organic solvent solution to the emulsion can be in the range of 7–15 percentage by volume.

PREFERRED EMBODIMENTS OF THE INVENTION

According to the method of the present invention by mixing and spraying an aqueous emulsion of a copolymeric resin as the "main solution" component, with an inert organic solvent solution (hardening agent-based) that contains a diisocyanate and polypropylene glycol along with an insect control chemical, complex reactions of the reactive isocyanate group, water, and the hydroxyl radical of the polypropylene glycol occur. The complex reactions form reacting soft to semi hard polyurethane resins while releasing gases within several to several tens of minutes that become the mixed resin foam coating layer in which the insect control chemical is uniformly dispersed in the main solution component. The method employs the relatively low viscous main solution component and has a superior spraying operability because a relatively small volume of low viscous organic solvent solution (hardening agent-based) is forcefully mixed in at the nozzle part of the sprayer. It is also beneficial, as it does not require operators to worry about soiling.

The method employs a main solution of copolymeric resin emulsion that contains vinyl acetate (VA) and an alkyl methacrylic ester (AE), in a proportion ranging from 55–85 and 15–45 parts by weight, respectively. If the VA content is less than 55 parts by weight (AE content is equal to or more than 45 parts by weight), the adhesion to soil can be reduced and increased use of AE is not beneficial. If the VA component exceeds 85 parts by weight (equal to or less than 15 parts by weight AE), the layer formed tends to be rigid and less flexible, which is not desirable because it can be easily cracked and split by vibration over time. The preferred weight proportion range of VA and AE is 60–80: 20–40 and the most desirable is 65–75: 25–35.

The AE monomer used to form the above copolymeric resin can be acrylic and methacrylic acid based alkyl ester group, and alkyl radical with four carbons or more are more practical. Desirable representative examples are n-butyl acrylate and 2-ethyl hexyl acrylate, and the latter is more desirable. In order to improve adhesion to soil, flexibility, tensile strength and other physical properties, a small volume, which is about equal to or less than 30% of total weight of VA and AE, of other copolymeric monomers can be incorporated into the copolymeric resin. Such copolymeric monomers include, for example, t-monocarboxylic acid ester group. Other known copolymeric monomers can also be incorporated as long as they do not materially inhibit the functions of the coating layer.

VA-AE based copolymers with a desirable proportion of each of the aforementioned copolymeric monomers are easily formed by a known emulsion polymerization in a water medium. In polymerization, aqueous emulsions with solid content density of 40–50 percentage by weight level are generally obtained. The emulsion can be diluted to an appropriate density, for instance, 15–20 percentage by weight resin solids part, to be used as the main solution. In the method, various additives are added to the VA-AE based copolymeric resin emulsion before it is mixed with a hardening agent-based solution. Such additives would be substances known to be useful in forming an under floor insect control soil coating resin foam layer, such as color pigments, anti foaming agents, mold proof agents, viscosity adjusting agents, aromatics, and plasticizers. A relatively small amount of these additives can be selectively incorporated.

Hardening agents used in the method can be non aqueous solutions in which the diisocyanate (DIC) and polypropylene glycol (PPG) are dissolved in an inert organic solvent. When mixed with water, isocyanate radicals react complexly and PPG forms a soft to semi hard polyurethane resin. Appropriate proportion ranges are 5–15 parts by weight DIC and 85–95 parts by weight PPG. If DIC is less than 5 parts by weight (PPG is equal to or more than 95 parts by weight), hardening can take a longer time causing the liquid to dribble, which is not desirable because the thickness of hardened coating layer then becomes inconsistent due to running of the liquid into lower portions of the soil. If DIC exceeds 15 parts by weight (PPG is equal to or less than 85 parts by weight), the reaction speed can be increased and a rigid foam coating can be formed. The desirable proportion of DIC and PPG is 10–14: 86–90 parts by weight range.

Appropriate DICs used in the invention include 2,4-tolylenediisocyanate, 4,4'-diphenylmethane diisocyanate, dianiline diisocyanate, hexamethylene diisocyanate, metaxylene diisocyanate. These are normally used singularly, but two or more can be selectively combined for applications. Tolylene diisocyanate (TDI) is industrially and applicably desirable.

PPG is a condensate of propylene glycol described by the chemical formula of $HO-[CH_2-CH(CH_3)-O]_n-H$, and normally has a relatively low molecular weight ranging around 3000–1000. PPG of the formula above has the number of propylene oxide (n) in the 20–70 level. If the molecular weight of PPG is too large, it can increase the viscosity of the hardening agent-based organic solvents and may delay urethane forming reaction, thus it is not always convenient. If the molecular weight of PPG is too low, it reduces the stability of the hardening agent-based solution, thus it is not perfectly desirable either. Appropriate molecular weight may vary slightly depending on the type and amount of DIC being mixed in.

Both DIC and PPG, which comprise the hardening agent, are dissolved in chemically nonreactive or inactive organic solvents. Inert organic solvents that can dissolve both ingredients include the ketone solvent group, such as dimethyl ketone, methyl ethyl ketone, and diethyl ketone, the aliphatic ether solvent group, such as dipropyl ether and methyl propyl ether, the lower aliphatic lactone solvent group such as butyl lactone, and the hydrocarbon solvent group. These inert organic solvents can be used singularly or in combinations of two or more. Mixtures of DIP and PPG in the aforementioned proportion are dissolved in these organic solvents and the viscosity is adjusted appropriately for applications. Applicable viscosity of such hardening agents, in relation to the total volume of DIC and PPG, usually can be within the range of 60–80 percentage by weight.

The insect control components used in the method are known chemical substances for controlling termites and other insects injurious to wood. These include chlorpyrifos, phoxim: 0,0-diethyl-0-($\alpha$-cyano benzyliden amino) thiophosphate, perhymetholyne: 3 phenoxy benzyl= (IRS.3RS)-(IRS.3RS)-3-(2,2-dichlorovinyl)-2,2-dimethyl cyclopropane carboxylate, ethophenprox: 2-(p-ethoxyphenyl)-2-methylpropyl-3-phenoxy benzyl ether, biphentoline: (2-methyl[1,1-biphenyl]-3-yl)methyl-3-(2-chloro-3,3,3-trifluoro-1-propenyl)-2,2-dimethylcyclopropane carboxylate, silafluophen: (4-ethoxyphenyl)[3-(4-fluoro-3-phenoxyphenyl)propyl] (dimethyl)silane, and pyresroid. Other well known insect control chemicals can be applied, as well.

Two or more of these insect control formulas can be mixed in this application. A single chemical appropriate for a subject insect, however, is normally used for each application. A fixed amount of the chemical is added to the main solution or to the hardening agent-based solution before the two are combined. It is normally added to the main solution, the copolymeric resin aqueous emulsion. It is important to embed enough concentration of insect control chemical in the layer to prevent termites and the like from eating through the layer and entering the under floor space. The appropriate amount depends on the chemical type and the insecticide effects. It is normally within the range of 2–4 percentage by weight of the total weight of the resin mix.

In the method of the invention, the hardening agent solution and the main solution which is the resin emulsion containing the insect control chemical are not truly compatible. It is possible, however, to form a precisely compartmentalized uniform mixture by forcefully and physically mixing them at a nozzle part of a sprayer. The resin solids content concentration of the main solution of VA-AE copolymerized resin emulsion in this mixture, as stated earlier, is adjusted in the range of 15–20 percentage by volume in consideration of the relatively low viscosity of the hardening agent-base organic solvents and the mixing operability. At the nozzle, the highly viscous solution comprising the hardening agent can be supplied at 7–15 percentages by volume of the aqueous resin emulsion. Too large or too small a percentage can be undesirable because the mixed resin foam may run before hardening or will not obtain relatively appropriate flexibility, hardness, non contraction property, or physical strength. The preferred range is 8–12 percent by volume.

Before mixing and spraying the mixture, the under floor ground surface must be flattened. Normally, about 450–600 ml of the main solution emulsion and about 10% volume of hardening agent in relation to the main solution volume per square meter are sprayed against the ground surface. The sprayed mixture forms soft to semi hard urethane as the isocyanate radical of DIC reacts with emulsion medium and PPG releasing a gas, and hardens to form a foam layer which is comprised of a substantially homogeneous mixed resin with the aforementioned copolymeric resin. The amount of mixture sprayed varies slightly depending on the nature of the soil, such as clayey or sandy; slightly more for sandy soil. The thickness of the formed coating layer also varies depending on the soil or foaming condition, but it is applied to form about 1–3 mm thickness when dried.

Forceful mixing of the main solution emulsion and hardening agent-based solution is done instantaneously at a mixing chamber located at a nozzle of a sprayer. The main emulsion, which contains the insect control chemical, is injected in the main pipe of the sprayer by applying pressure and allowing the velocity of the flow to draw hardening agent-based solution from a supplying pipe by utilizing the principle of atomization. The proportion of the mix can be controlled by selecting the feeding speed or the pressure of the main emulsion to the main pipe and adjusting the size of the suction opening for the hardening agent-based solution accordingly. Sprayer, or equipment described in Japanese Laid-Open Utility Model No. 3-40369 (1991) and Japanese Laid-Open Utility Model No. 4-915 (1992), can be conveniently used as the sprayer that forcefully mixes and sprays the two solutions.

The forcefully mixed solution is ejected from the nozzle by its own force and sprayed almost uniformly onto the ground surface. The sprayed solution hardens as the isocyanate chemically reacts while releasing a gas, and forms a mixed resin foam coating layer which is substantially homogeneous with the urethane and VA-AE-based copolymer. The coating layer formed in this fashion is a relatively thin resin foam sheet as described above. The layer, however, usually has 80–90% gas barrier property (moisture-proof property) and completely prevents termites and other microorganisms from migrating from soil to under floor space. The layer also substantially prevents moisture in the soil from evaporating, thus effectively preventing wood rot of structure posts and the like. In addition, such resin coating barrier keeps under floor air temperatures cooler in summer and warmer in winter, as compared to the external air. Thus, the foam could be utilized in the air cycle system of houses and conveniently incorporated during the construction of energy conserving houses.

Hardening speed of the sprayed solution is generally fast if the surrounding temperature is high and slow if the temperature is low. DIC's urethane forming reaction speed can also be controlled by organic solvents in the hardening agent-based solution. Selection and combination of such organic solvents can be easily determined in advance through simple experimentation. Desirable hardening time, judging from on site work conditions, can be usually 15 to 30 minutes after spraying. Work is most efficiently conducted if hardening time in that range is factored in. When forming an insect control layer with this method, the surfaces of columns and beams are preferably treated by a traditional insect control surface treatment immediately before or at the time of spraying. Because the mixed resin foam barrier formed in this invention is thin and light, it can be easily cut with a sharp knife or a cutter and removed if further insect control treatments are necessary.

The insect control mixed resin foam barrier formed by the method of the invention not only embeds insect control ingredients uniformly and in a stable manner, but also functions as a stable insect control gas barrier layer for a long time period because of its appropriate flexibility and non contraction properties that prevent cracks and gaps.

EXAMPLES

The following are specific explanations of the invention's termite control method using application examples. In the examples, unless otherwise specified, parts and percentages are those by weight. Also, the moisture-proof ability of the mixed resin foam barrier was measured in accordance with a moisture permeability test method for moisture proof packaging materials used in the JIS (Japan Industrial Standard) Z 0208. The chemical immobilization was determined by analyzing the amount of chemical (density) in the barrier. Flexibility and non contraction properties were qualitatively determined by observing the existence of cracks.

EXAMPLE 1

A co-polymeric resin aqueous emulsion obtained by emulsifying and co-polymerizing 65% vinyl acetate and 35% of equal volume mixture of butyl acrylate and 2-ethyl hexyl acrylate was diluted with water to adjust its resin concentration to 16%. The main solution was prepared by adding 2 kg of chlorpyrifos as an insect control chemical, 3 kg of titanium oxide white pigment containing a small portion of carbon black (gray colored), a small amount of antifoaming and mold proof agents to 200 kg of the emulsion. The hardening agent-based solution, with 70% hardener, was prepared by dissolving 9% of 2,4 tolylenediisocyanate (TDI) and 91% of PPG in the mixed solvent, in equal volume, of methyl ethyl ketone and gamma-butyl lactone. The main solution and the hardening agent-based solution are forcefully mixed and sprayed by using the equipment described in the Japanese Laid Open Utility Model No. 3-40369 (1991) onto the under floor soil surface. The sprayer was adjusted to mix the main solution and the hardening agent-based solution at a volume ratio of ten to one. The mixture was sprayed over the ground surface of a wooden house with a floor area of about 30 square meters. The amount sprayed per square meter was 2.5 liters of the main solution and 250 milliliters of the hardening solution.

The sprayed resin mixture layer hardened almost completely in about 15 minutes as the DIC chemically reacted to become a polyurethane foam while emitting a gas. The dried resin foam layer was about 2 mm thick. The insect control chemical component, chlorpyrifos, in the layer was measured periodically, from a year after the spraying to eight years after. Annual reduction of the content was equal to or less than 1%. No cracks or gaps were observed in the foam resin insect control layer and no rot or damage of the under floor wood members due to moisture or insects was observed after eight years.

Examples 2–3 and Comparative Examples 1–4

The main solution emulsion and hardening agent-based solution were prepared as follows.

Preparation of Main Solution Emulsion

Four types of main solution aqueous emulsion with different proportions of vinyl acetate (VA) and 2-ethyl hexyl acrylate (2EHA) were prepared and the same insect control chemical, pigments, anti-foaming and mold proof agents used in Example 1 were added to each emulsion in the same fashion. Each solution was diluted with water to have a 17% resin solidity content. Table 1 shows the weight distribution of each emulsion's copolymeric ingredients.

TABLE 1

| Main Solution Component | Main Component 1 | Main Component 2 | Main Component 3 | Main Component 4 |
|---|---|---|---|---|
| VA | 50 | 60 | 80 | 90 |
| 2EHA | 50 | 40 | 20 | 10 |

Preparation of Hardening Agent-Based Solution

Three types of hardening agent-based solution (Hardening components 1–3) were prepared by dissolving tolylenediisocyanate (TDI) and polypropylene glycol (PPG) with average molecular weight of 2000 in different proportions into an inactive organic solution comprised of equal volume of gamma-butyl lactone and methyl propyl ether. Total concentration of the TDI and PPG were adjusted to 70% for each solution. Table 2 shows the weight distribution of TDI and PPG.

TABLE 2

| Hardening Agent-Based Solutions | Hardening Component 1 | Hardening Component 2 | Hardening Component 3 |
|---|---|---|---|
| TDI | 4 | 10 | 16 |
| PPG | 96 | 90 | 84 |

The ground surface was sectioned into a number of one square meter sections. Combinations of main emulsions (Main Components 1–4) and a hardening solution (Hardening Component 2), and a main emulsion (Main Component 2) and hardening solutions (Hardening Components 1 and 3) were mixed at a proportion of ten (main solution component) to one (hardening solution component) and sprayed on each ground section by using the sprayer used in Example 1 to obtain a mixed resin foam layer that adhered to the ground. Each foam layer after drying was about 2 mm thick. The insect control chemical's immobilization property, the moisture proof property and the existence of cracks were determined. Table 3 shows the combinations of the main emulsion and hardening solution for each example.

TABLE 3

| | (CE: Comparative Example and EX: Example) | | | | | |
|---|---|---|---|---|---|---|
| | CE 1 | EX 2 | EX 3 | CE 2 | CE 3 | CE 4 |
| Main Solution | 1 | 2 | 3 | 4 | 2 | 2 |
| Hardening | 2 | 2 | 2 | 2 | 1 | 3 |

In each combination, the reduction of insect control chemical was less than several percentages after five years and the insect control chemical was satisfactorily immobilized. Comparative Example 1 was not so desirable because of a slight inferiority in adhesion to soil and cost of materials. Comparative Example 2's resin barrier was somewhat too hard, not so flexible enough as desired, and caused some cracks over time. Comparative Example 3 did not foam sufficiently and hardened slowly, causing the solution to run. Thus, it did not provide stable or high gas barrier property as desired because the thickness was somewhat inconsistent. Comparative Example 4 was relatively susceptible to deterioration from ultraviolet light, thus had some problems in the weatherproofing aspect. Barriers formed in Examples 2 and 3 did not have such problems described above and the barriers functioned as stable insect control layers for a long time period.

Example 4, Comparative Examples 5, 6

Using the aforementioned Hardening component 2 and Main component 2, the valve on the hardening agent-based solution suction pipe side of the sprayer was adjusted to vary the mixture proportions to form a mixed resin foam layer on the ground sections. Table 4 shows the distributions of mixed resin for each example.

TABLE 4

| | CE 5 | EX 2 | CE 6 |
|---|---|---|---|
| Main Component 2 | 100 | 100 | 100 |
| Hardening Component 2 | 5 | 10 | 20 |

Comparative Example 5's hardening speed was slower, causing somewhat insufficient foaming and the solution ran into low portions or valleys on the soil surface. The layer thickness was relatively inconsistent and did not provide a perfectly desirable gas barrier. Comparative Example 6 had more urethane resin foam than necessary and was relatively susceptible to deterioration from ultraviolet light. It needed to be replaced in a relatively short time period because it was not desirably stable over time.

The mixed resin foam insect control barrier formed by the method of the invention provides superior insect control chemical immobilization, gas barrier and crack proof properties. It prevents termites and other microorganisms in the ground from encroaching into the under floor space and also prevents moisture from permeating. The method safely maintains wooden residential structures over a prolonged time period and significantly contributes to social life.

What is claimed is:

1. An under floor insect control method for protecting structures from injurious insects comprising:

forming an asphalt-free mixed resin foam layer on a soil surface or under a floor of a structure by (1) forcefully mixing at a nozzle of a sprayer (a) an insect control agent, (b) an aqueous emulsion, of which 15–20 percent by weight is a solid resin component of a copolymer of vinyl acetate and alkyl methacrylate in a proportion ranging from 55–85 and 15–45 parts by weight, respectively, and (c) an inert organic solvent solution of a mixture of diisocyanate and polypropylene glycol in a proportion ranging from 5–15 and 85–95 parts by weight, respectively, which comprises an adjusted 60–80 percent by weight as a total volume of the diisocyanate and polypropylene glycol;

(2) spraying the said insect control agent, said aqueous emulsion and said inert organic solvent solution ingredients which have been forcefully mixed together onto said soil surface or under a floor of a structure; and (3) permitting sprayed ingredients to react to release gas within minutes and to form a mixed resin foam coating containing said insect control agent dispersed therein which is resistant to insects eating through the resulting barrier layer and which is resistant to moisture penetration with sufficient flexibility to prevent cracks and gaps.

2. An under floor insect control method according to claim 1, wherein the proportion of the inert organic solvent solution to the aqueous emulsion is in the range of 7–15 percentage by volume.

3. An under floor insect control method according to claim 1, wherein the alkyl methacrylate is butyl acrylate and/or 2-ethyl hexyl acrylate.

4. A method for controlling insect damage and protecting structures from injurious insects comprising, (1) providing a main solution comprising an insect control agent and an aqueous emulsion, of which 15–20 percent by weight is a solid copolymer resin containing 55 to 85 parts by weight vinyl acetate and a 15 to 45 parts by weight alkyl methacrylate and (2) a hardening agent solution including a mixture of diisocyanate and polypropylene glycol in a proportion ranging from 5–15 and 85–95 part by weight, respectively, which comprises an adjusted 60–80 percent by weight as a total volume of the diisocyanate and polypropylene glycol;

(3) forcefully mixing together the main solution and the hardening agent instantaneously at a mixing chamber located at a nozzle of a sprayer, and (4) forming a mixed resin foam coating layer containing said insect control agent dispersed therein by applying the resulting composition formed by said forcefully mixing to a soil surface.

5. The method according to claim 4, wherein the proportion of hardening agent solution to the main solution is in the range of 7–15 percentage by volume.

6. The method according to claim 4, wherein the alkyl methacrylate is butyl acrylate and/or 2-ethyl hexyl acrylate.

7. A buffer layer produced by the method of claim 1.

8. The method according to claim 4, wherein the forcefully mixing of the insect control agent, the main solution and the hardening agent solution is carried out at a nozzle and the resulting foamable composition formed at the nozzle is sprayed onto soil under a floor of a structure to thereby form a foamed coating containing the insect control agent dispersed therein.

9. The method according to claim 4, wherein said insect control agent is present in sufficient amount to prevent insects from eating through said layer.

* * * * *

UNITED STATES PATENT AND TRADEMARK OFFICE
CERTIFICATE OF CORRECTION

PATENT NO. : 5,902,597
DATED : May 11, 1999
INVENTOR(S) : Iwakawa, et al.

It is certified that error appears in the above-identified patent and that said Letters Patent is hereby corrected as shown below:

ON THE COVER PAGE

Please add the foreign priority data as follows:

-- [30]    Foreign Application Priority Data

Mar. 27, 1995 [JP]   Japan . . . . . . . . . . . . . . . . 7-068153 --.

Signed and Sealed this

Nineteenth Day of December, 2000

Attest:

Q. TODD DICKINSON

*Attesting Officer*   Commissioner of Patents and Trademarks